(12) United States Patent
Lex

(10) Patent No.: US 7,566,894 B2
(45) Date of Patent: Jul. 28, 2009

(54) DEVICE AND METHOD FOR THE QUANTIFIED EVALUATION OF SURFACE CHARACTERISTICS

(75) Inventor: Konrad Lex, Rossmoosweg (DE)

(73) Assignee: BYK Gardner GmbH, Geretsried (DE)

( * ) Notice: Subject to any disclaimer, the term of this patent is extended or adjusted under 35 U.S.C. 154(b) by 0 days.

(21) Appl. No.: 11/139,027

(22) Filed: May 26, 2005

(65) Prior Publication Data

US 2006/0065857 A1    Mar. 30, 2006

(30) Foreign Application Priority Data

Jul. 30, 2004    (DE) .................... 10 2004 037 040

(51) Int. Cl.
*G01N 21/86*    (2006.01)
*G02B 11/24*    (2006.01)

(52) U.S. Cl. ..................... 250/559.4; 356/601

(58) Field of Classification Search ............. 250/559.4, 250/559.16, 339.11, 341.8; 356/237.1, 237.9, 356/237.2, 600, 601

See application file for complete search history.

(56) References Cited

U.S. PATENT DOCUMENTS

| | | | | |
|---|---|---|---|---|
| 4,629,319 A | * | 12/1986 | Clarke et al. ............. | 356/237.2 |
| 4,801,809 A | * | 1/1989 | Burk et al. ............. | 250/559.04 |
| 5,477,332 A | * | 12/1995 | Stone et al. ................. | 356/613 |
| 6,166,393 A | * | 12/2000 | Paul et al. ............. | 250/559.08 |
| 6,239,436 B1 | * | 5/2001 | Parker et al. ............. | 250/341.8 |
| 6,271,878 B1 | * | 8/2001 | Sera ........................... | 348/164 |
| 6,542,248 B1 | * | 4/2003 | Schwarz ..................... | 356/600 |
| 7,019,822 B1 | * | 3/2006 | Doak et al. .................... | 356/73 |
| 2003/0212506 A1 | * | 11/2003 | Sundman et al. ............. | 702/40 |
| 2003/0229458 A1 | * | 12/2003 | Alfano et al. ................. | 702/40 |
| 2003/0234925 A1 | * | 12/2003 | Hunt ....................... | 356/237.1 |
| 2005/0001166 A1 | * | 1/2005 | Sanzari ................. | 250/339.11 |

FOREIGN PATENT DOCUMENTS

| JP | 10260141 A | * | 9/1998 |
|---|---|---|---|
| JP | 2001201474 A | * | 7/2001 |

* cited by examiner

*Primary Examiner*—Thanh X Luu
(74) *Attorney, Agent, or Firm*—Greer, Burns & Crain, Ltd.

(57) ABSTRACT

A device for the quantified evaluation of surface characteristics including a first radiation structure which is arranged in a first predetermined angle with respect to a surface to be analyzed and which directs radiation onto the surface to be analyzed, wherein the radiation directed onto the surface has at least one component with wavelengths in the infrared area, a detection apparatus arranged in a second predetermined angle with respect to the surface to be analyzed detecting the radiation radiated onto the surface and being thrown back from it.

15 Claims, 3 Drawing Sheets

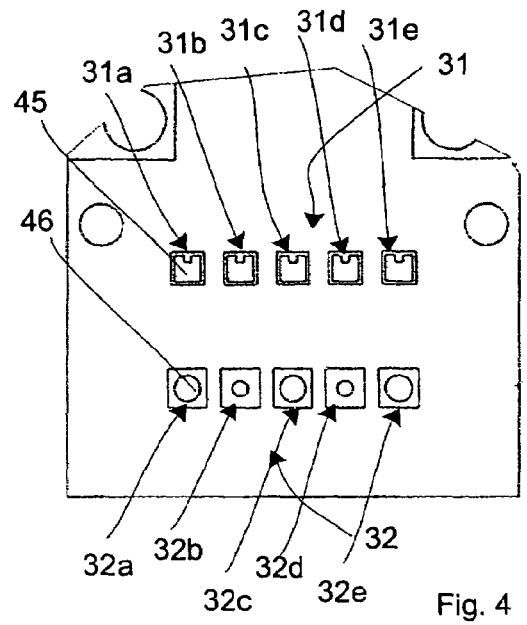
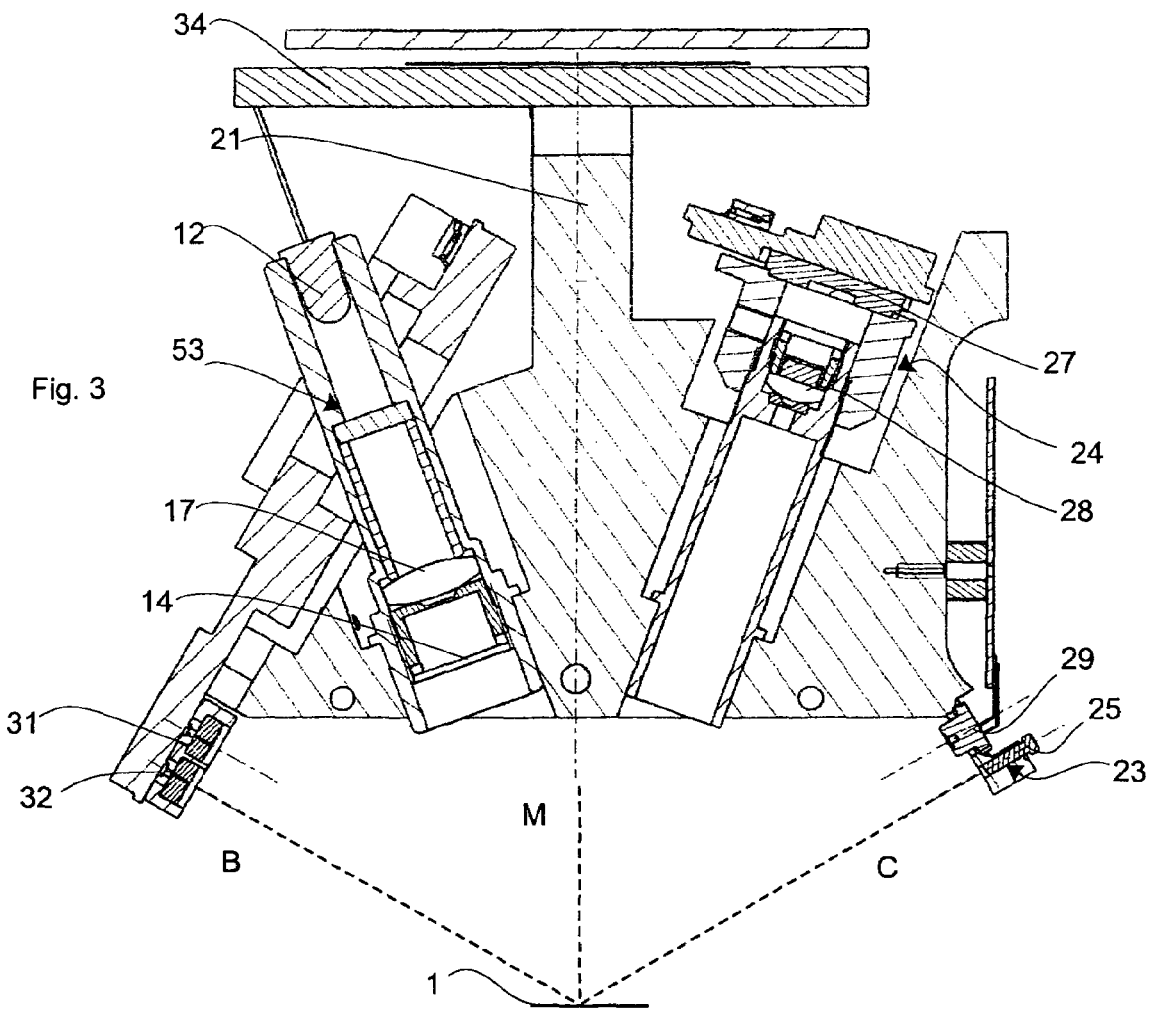

DEVICE AND METHOD FOR THE QUANTIFIED EVALUATION OF SURFACE CHARACTERISTICS

BACKGROUND

The present invention relates to a device and a method for the quantified evaluation of surface characteristics.

The invention is described in respect to varnished surfaces in particular in respect to the surfaces of bodies of automobiles. However it is pointed out that the present invention can also be used with other surfaces.

In numerous technical products the condition of the visible surfaces is a crucial characteristic for the overall impression of the product.

Automobiles are usually provided with a high gloss varnishing whose gloss characteristic value is normally far higher than the gloss characteristic value of other surfaces, for instance, furniture surfaces and the like. The high gloss of the varnishing used and the relatively big surfaces require an exceptionally careful preparation of the surfaces to be varnished and a very careful application of the varnish. In order to identify quality defects of varnished automobile body surfaces devices are known from the state of the art which permit an objective characterization or evaluation of the surfaces by the evaluation of light radiated thereon. By means of these devices, for instance, unevenness in the varnish layers can be detected and evaluated quantitatively.

The varnishes typically used in the automobile industry not only have an outer varnish layer but basic varnish layers lying under said outer varnish layer. In order to produce qualitatively acceptable final layers it is necessary to also check the condition of the respective basic varnishes. In doing so, the problem appears that these basic varnishes relatively weakly reflect light radiated on them and hence an evaluation of this basic varnish is very elaborate.

Hence it is an objective of the present invention to create a device which also permits an evaluation of the basic varnishes.

SUMMARY OF THE INVENTION

According to the invention this is achieved by the subject matter of claim 1. Advantageous embodiments and improvements are subject matter of the dependent claims.

The device according to the invention for the quantified evaluation of surface characteristics has a first radiation means which is arranged in a first predetermined angle with respect to a surface to be analyzed and which directs radiation onto the surface to be analyzed. At the same time the radiation directed onto the surface has at least one component with wavelengths in the infrared area. Furthermore a detection means is provided in a second predetermined angle with respect to the surface to be analyzed which detects the radiation radiated onto the surface and thrown back therefrom.

As infrared radiation such radiation or such light is understood which has wavelengths which are longer than the wavelengths of the visible light. However preferably the wavelengths used are shorter than the structures to be analyzed. As predetermined angle the solid angle is understood in which the radiation means or the detection means is arranged with respect to the surface to be analyzed.

As thrown back radiation the radiation is understood which is reradiated from the surface after it has been directed onto the surface thus, in particular, however not exclusively, the reflected, diffracted or scattered radiation.

This solid angle is composed by a pair of angles which is suitable to determine the position of the respective means with respect to the surface to be analyzed.

As radiation which consists of several components with different wavelengths such radiation is understood which has light of different wavelengths or different wavelength areas.

As directing radiation onto a surface it is understood that at least a part of the emitted radiation reaches the surface. This radiation itself needs not to be collimated or directed but can also be more or less divergent or diffused.

Preferably the detection means detects the radiation radiated from the first radiation means onto the surface and reflected therefrom. This means that the detection means is arranged such that it detects the light that is radiated in a predetermined angle of incidence onto the surface and is reflected according to the reflection law.

In another preferred embodiment the first radiation means is implemented as a point light source. As a point light source such a light source is understood which radiates light with a high divergence. Such a light source can be achieved by the usage of small apertures. However, preferably the first radiation means has an optical fiber which directs the light onto the surface to be analyzed. The usage of a fiber has the advantage that the usage of additional apparatuses can be waived since the fibers themselves have a very small cross section and in this way generate very divergent light.

By the usage of a point light source an enlarged picture of the surface to be analyzed is enabled in particular in the detection plane. Preferably additional elements as lenses and the like can be renounced.

In a further preferred embodiment the high divergence is generated by lenses, in particular, however, not exclusively lenses with a short focal length. Such a lens can be used in conjunction with an optical fiber but also independently thereof.

In a further preferred embodiment the detection means has radiation limitation elements. These preferably concern apertures. These apertures can be chosen with fixed or variable aperture cross section.

In another preferred embodiment the detection means permits a location resolving detection of the radiation impinging on it. This means that the detection means not only evaluates the radiation with respect to its radiation intensity, but beyond that, permits to detect the radiation resolving the location. For this purpose the detection means preferably has plane image receiving means as, for instance, CCD chips and the like.

In another embodiment the detection means does not permit location resolving detection of the radiation, in this case the detection means has photo-sensitive elements like photo sensors or photo electric cells.

In another preferred embodiment the detection means is also sensitive for the irradiation of infrared light.

In another preferred embodiment the radiation means has several light sources with different emission spectrum. Thus, for instance, individual light sources can be provided which radiate light in the visible area while further light sources emit light in the infrared wavelength area.

Preferably the radiation means additionally has several light sources which are designed such that the emission spectrum of the light emitted by these light sources substantially covers the complete area of visible light or parts thereof and at least individual areas of the infrared light. By means of this substantially complete coverage a most precise reproduction of predetermined light conditions, as for instance white light, can be carried out. On the other hand, by using several radiation sources, it is also possible to light up the surface selectively with light of a predetermined wavelength and to evaluate the radiation accordingly.

Preferably the detection means is designed such that it is sensitive over substantially the whole visible area and at least parts of the infrared wavelength areas. For instance Germanium can be used as sensor material.

In another preferred embodiment at least one light source is a laser. For this purpose, for instance, semi-conductor lasers can be used which deliver a continuous radiation. However, also LEDs and the like can be used as a light source.

In a further preferred embodiment several radiation means are arranged in different solid angles with respect to the surface to be analyzed. At the same time these several radiation means can have different emission spectra, partially in the visible and partially in the infrared area.

In another preferred embodiment another radiation means radiates diffuse light onto the surface to be analyzed. Therein this diffuse light can be achieved by the usage of depolished glass disks or scattering disks or similar things.

In another preferred embodiment the detection means has a plurality of detectors. Therein the individual detectors can be arranged in a predetermined manner with respect to one another, for instance, on a line or the like. Preferably also at least two detectors have different sensitivities for different radiation, i.e. radiation of different wavelengths.

In another preferred embodiment several substantially congeneric detectors are arranged on a substantially straight line. In this way an evaluation of the light impinging on these detectors along the line can be carried out. Preferably the device can be shifted or moved with respect to the surface to be analyzed in this direction.

In another preferred embodiment a first number of detectors with sensitivities in a first wavelength area is arranged in one line and, basically offset thereto, a second number of detectors for the visible wavelength areas in a second line. In this way it is for example possible to arrange a predetermined number of first detectors for the infrared wavelength areas in a line and a second number of detectors for the visible wavelength areas in a second line which is substantially parallel to the first line.

In another preferred embodiment the device has motion means which permit a motion of the device with respect to the surface to be analyzed. For example these motion means can be wheels or the like.

Preferably the motion means are connected with distance measuring means which permit to determine the covered distance of the device with respect to the surface to be analyzed.

Preferably the device has an evaluation means preferably connected with the detection means which evaluates the measuring values determined out of the received radiation by the detection means. Preferably the measuring values determined in the context of the evaluation are correlated to one another by carrying out averaging or comparable mathematical operations.

Furthermore, the measuring values are associated with measuring data which give explanation about the relative position of the device with respect to the surface to be analyzed.

The invention is further directed to a method for the quantified evaluation of surfaces. Therein, in a first method step, radiation which has at least one component in the infrared wavelength area is radiated onto the surface to be analyzed. In another step of the method the light reflected by the surface to be analyzed is received by detection means and is preferably evaluated. More precisely the radiation impinging onto the detection means is converted into a characteristic electronic signal and this being evaluated.

Preferably the device according to the invention is moved with respect to the surface to be analyzed during a measuring process and in this way a plurality of measuring values is recorded. Preferably during the motion of the device according to the invention with respect to the surface to be analyzed a measuring value is recorded at predetermined locations respectively which altogether leads to a plurality of measuring values. The evaluation of this plurality of measuring values permits characterization of the quality of the surface to be analyzed. By means of a distance measuring means the position of the device with respect to the surface to be analyzed can be determined and in this way the measuring values can be assigned to a certain geometrical location.

Preferably first a plurality of measuring values is recorded, which is evaluated, the recorded measuring values are referred to as brightness measuring values. In the following evaluation step, surface measuring values are formed out of the brightness measuring values by taking into account a first number $n_1$ of preceding measuring values and a second number $n_2$ of succeeding measuring values. Therein, preferably the number $n_1$ equals the number of $n_2$ measuring values. Therein, at first, a number of $n_1$ brightness measuring values before the first measuring value to be determined is recorded and, after the last surface measuring value, a further number of $n_2$ brightness measuring values. Depending on the chosen number of measuring values $n_1$ and $n_2$, a greater number of long wave surface defects or short wave surface defects can be detected. Preferably the individual measuring values are also assigned to the respective location of the measurement which can, for instance, be retraced by the distance measuring means.

Further advantageous embodiments of the present invention can be seen from the drawings.

BRIEF DESCRIPTION OF DRAWINGS

Therein the respective figures show:

FIG. 3 is a device according to the invention for the quantified evaluation of surfaces and;

FIG. 4 is a section of the detection means for the device according to the invention in FIG. 3;

DETAILED DESCRIPTION

Figure 1:
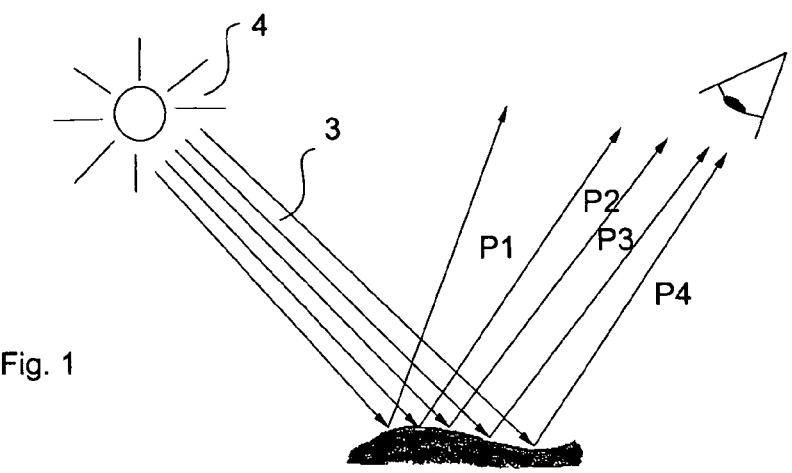
FIG. 1 is a schematic illustration of the object of the patent.
Figure 2A:
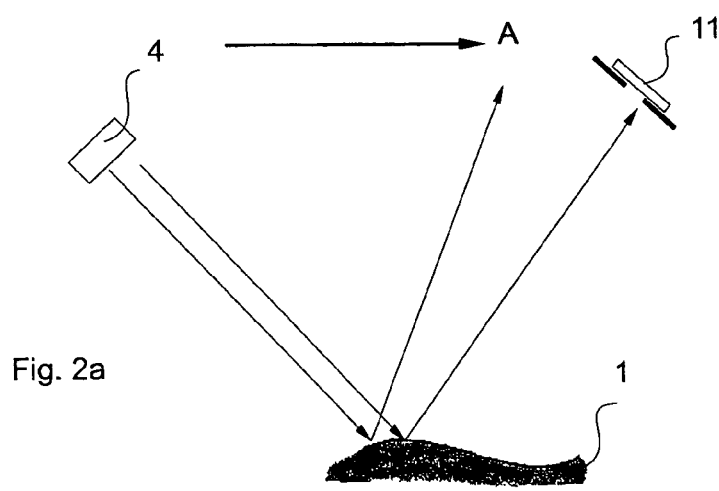
FIG. 2a is a schematic representation of the illustration of the principle of the measurement method.
Figure 2B:
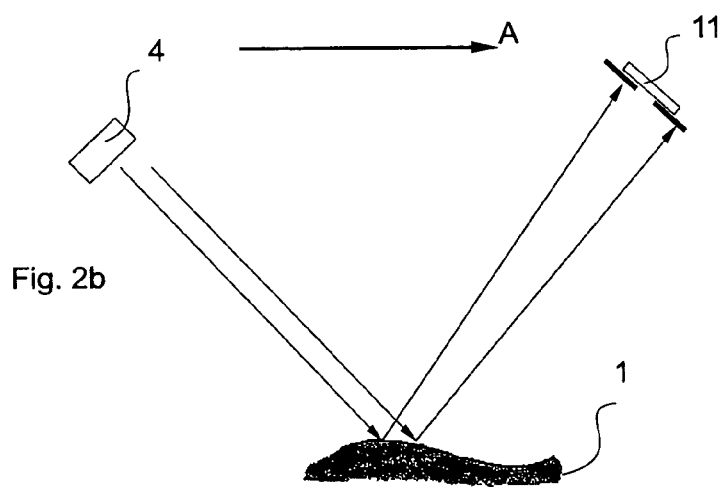
FIG. 2b is further schematic representation of a further illustration of the principle of the invention.
Figure 2C:
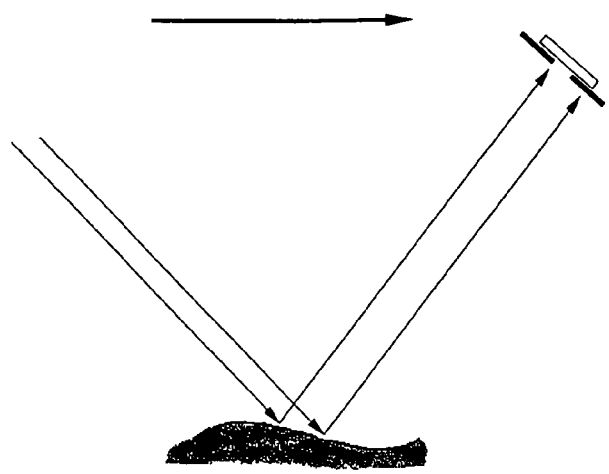
FIG. 2c is a further schematic representation for the illustration of the principle of the measurement method.
Figure 2D:
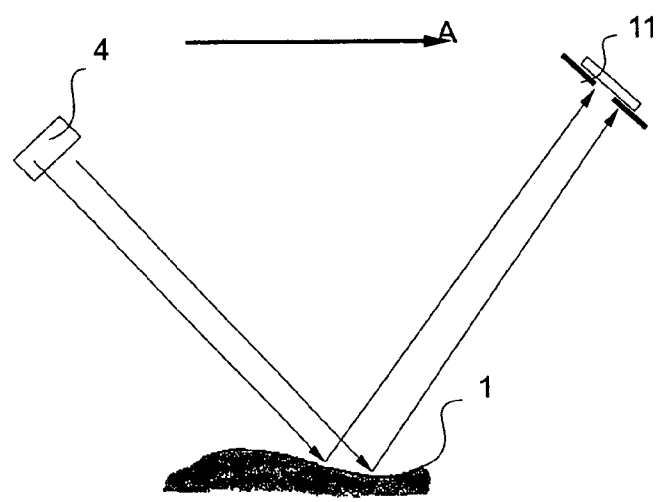
FIG. 2d is a further schematic representation for the illustration of the principle of the measurement method.
Figure 2E:
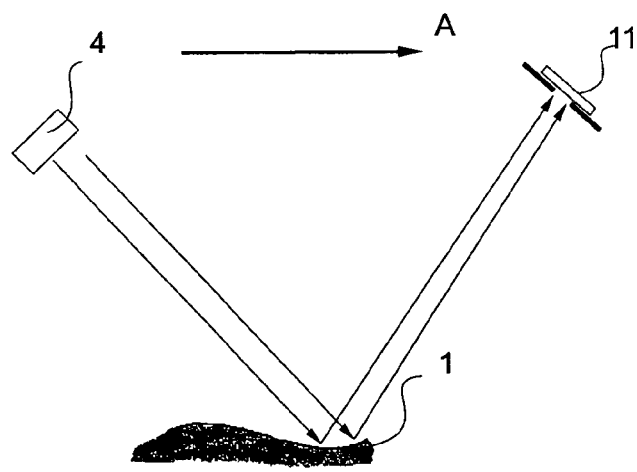
FIG. 2e is a further schematic representation for the illustration of the principle of the measurement methods.

In FIG. 1a schematic representation for the illustration of the problem forming the basis of this invention is shown. Radiated light 3 from a light source 4, as for example from the sun, impinges onto a surface 1. Due to the curved characteristic of the surface however, the light substantially is not reflected in parallel to the direction of an observer 6, but, according to the curvature of the surface, along the individual arrows P1 to P5. Due to this phenomenon the observer gets the impression of a not completely plane surface or of the optical effect also known as "Orange Peel".

FIGS. 2a to 2e illustrate the principle of the invention. Therein, the device according to the invention is shifted along the arrow A with respect to the surface 1 to be analyzed. The light originating from the light source 4 is reflected by the surface 1 to be analyzed and thrown onto a detection means 11. Depending on the respective curvature of the surface 1, more or less light gets onto the detection means 11. This is shown in FIGS. 2a to 2e, in which, according to the impinging point of the rays of light on the surface 1, the throw back rays have different directions and thus, the light impinges onto the detector 11 with different intensity. By means of a slow scan of the surface to be analyzed along the arrow A, in this way an image of the curvature characteristic of the surface can be achieved.

In a preferred embodiment the detection means 11 permits a location resolving representation of the rays impinging on it, i.e. not only a resolution in terms of intensity of the radiation but a location resolving image. In this way, more precise information about the surface to be analyzed is achieved.

In a preferred measurement method the device is shifted along the arrow A with respect to the surface 1 to be analyzed and a plurality of measurement values is recorded respectively. Therein, the device can use rubber wheels or rubber rollers which directly detect the relative motion of the surface 1 and the device and thereby secure the exact geometrical assignment of the measurement point to the surface.

By means of recording a plurality of measurement values, on the one hand, a recurring unevenness can be detected in short distances (so called short wave unevenness). By the evaluation of a plurality of measurement points, however, for example by usage of suitable averaging, also long wave recurring unevenness can be recognized.

Preferably a classification in several wavelength areas, as for example five wavelength areas, can be carried out. It has been observed that such a classification guarantees a very precise representation of the surface to be analyzed.

Thus a measurement can be evaluated with for example 50, 40, 30, 20 or 10 preceding and succeeding measurement points, wherein with a higher number of measurement values the long wave surface defects can be detected better and with a smaller number the short wave surface defects can be detected better.

In order to also analyze the basic varnish as mentioned at the beginning having only a small reflectivity in the visible area of light, according to the invention the usage of infrared light is suggested.

FIG. 3 shows the device according to the invention. This has a housing 21 in which both the radiation means 23 as well as the detection means 32 are accommodated. Therein, the radiation means and the detection means are arranged in a predetermined angle with respect to the surface 1 to be analyzed. As respective angle in which the means are arranged above the surface to be analyzed the solid angle is understood which is formed between the perpendicular bisector 14 of the surface to be analyzed and the axis B and C which run through the center of the radiation and detection means.

The radiation means has a light source (not shown). The reference sign 32 refers to a feed through means in which a light guide (not shown), as for example an optical fiber, can be fed through. As light source, in particular, but not exclusively, an IR-laser or a Super LED with an emission spectrum in the infrared area can be used. In the embodiment shown in FIG. 4 a Super LED with an emission wavelength in the area of 800 nm-1700 nm, preferably in the area of 1550 nm, is used.

The optical fibers known from the state of the art have a so-called core which is the actual light guiding medium. This core is surrounded by a cladding which fulfills an isolating function by preventing lateral leakage of radiation out of the core through total reflectance. Nevertheless the light enters into the cladding already at the entry into the fiber and exits it at the end of the fiber when the optical fiber is guided substantially straight over longer distances.

For this reason, the optical fiber is arranged curved before the entry into the feed through means, preferably rolled up on a length of about 2 m to 3 m to prevent a leakage of light out of the cladding at the end of the fiber.

The reference sign 29 refers to a further radiation means. This radiation means has a light source which radiates light in the visible wavelength area. In the embodiment shown in FIG. 4 an emission wavelength of 650 nm is used.

Preferably the radiation means 29 radiates a light spot which is reflected by the surface and received by the detection means 31. Preferably the detection means 31 is a detection means which permits a location resolving representation of the light impinging on it, preferably a color camera.

The detection means 32 is at least also sensitive for radiation in the infrared area. Preferably also the detection means 32 is a detection means which allows a location resolving representation of the light impinging on it.

The reference sign 53 refers to another radiation means and the reference sign 27 to another detection means which serve to the evaluation of the surfaces of the finished varnishing layers in the embodiment shown in FIG. 4. Through these means gloss measurements are carried out.

The values achieved through these gloss measurements are used for the correction of those results which are achieved through the measurements with infrared light presented above.

In the radiation means 53 at least one light source 12 is accommodated. For the generation of such light, for instance, semi-conductors, laser diodes or the like can be used. The light is directed through a lens system 17 onto the surface to be analyzed.

The radiation means 53 and the detection means 24 are substantially arranged such that the light irradiated from the radiation means is substantially reflected by the surface 1 to be analyzed onto the detection means 24. Besides the light source 12, the radiation means 53 can have further light sources which preferably cover the whole visible area of the spectrum or parts thereof.

The detection means 24 has a detection element 27 which detects the radiation impinging on it. For this purpose the detection means preferably also has a lens system 28. In a preferred embodiment also a color camera is used as a detection means.

Above that, however, also further detection means (not shown) can be provided which detect the light thrown by the surface.

According to another embodiment also single or several radiation means (not shown) can irradiate diffuse light and for this purpose be provided with scattering disks depolished glass disks or the like. Reference sign 34 refers to a display for the evaluation of the measured values.

FIG. 4 shows a detector which is composed by the detection means 31 and 32. These have first detectors 32a to 32e and second detectors 31a to 31e. In the shown embodiment, the respective detectors of the detection means 32 and 31 are arranged in a line. Preferably the respective detectors of the detection means 32 and 31 are substantially perpendicular to the direction in which the device is moved with respect to the surface 1. The lower plurality 32 has five single detectors in this embodiment which are at least also sensitive in the infrared wavelength area. The upper plurality 31 has five single detectors in this embodiment which are in particular sensitive in the visible area. The individual detectors 31*a* to 31*e* have aperture means (not shown) and preferably filters (not shown), in particular band filters, which in the embodiment shown have substantially equal optical apertures. The single detectors of the detection means 32 and 31 have aperture means with alternating different optical apertures. The detectors itself can also have different detection surfaces in order to selectively evaluate the light of only one radiation source. This selection is however not compelling, also different optical apertures can be provided. Also computer-aided aperture controls or also sensor arrays with programmable apertures can be used.

The invention claimed is:

1. A device for the quantified evaluation of a curved surface, comprising:
    a housing;
    first radiation means which is arranged in a first predetermined angle with respect to the curved surface to be analyzed and directing non-collimated radiation onto the curved surface to be analyzed, said first radiation means being configured to emit light in the spectrum of infrared light;
    at least one second radiation means directing radiation onto the curved surface to be analyzed and configured to emit light in the spectrum of visible light; and
    a detection means arranged in a second predetermined angle with respect to the curved surface to be analyzed detecting the radiation irradiated onto the curved surface and reflected back from it and analyzing light intensities associated with the reflected radiation, said first radiation means and said detection means being positioned in said housing;
    wherein said device is moveable in a predetermined direction along, and in the direction of the curved surface to be analyzed;
    wherein said detection means includes a plurality of detectors each being arranged in a straight line oriented substantially perpendicular to said predetermined direction, and a plurality of substantially congeneric detectors being arranged along one of said straight lines, said congeneric detectors having similar sensitivities with respect to detecting said radiation, such that a curvature characteristic of the curved surface is obtained by analyzing the light intensities detected by said detection means moving in said predetermined direction, the detected light intensities varying in direction with the curvature characteristic of the analyzed surface.

2. The device according to claim 1 wherein the first radiation means is carried out as point light source.

3. The device according to claim 1 wherein the first radiation means has an optical fiber.

4. The device according to claim 1 wherein the detection means has at least one radiation limiting element.

5. The device according to claim 1 wherein the detection means has a filter element.

6. The device according to claim 1 wherein the detection means has several apertures.

7. The device according to claim 1 wherein the detection means permits a location resolving detection of the radiation detected by it.

8. The device according to claim 1 wherein the first radiation means has several light sources with at least partially different emission spectra.

9. The device according to claim 8 wherein at least one light source is a laser.

10. The device according to claim 1 wherein said at least one second radiation means directs diffuse light onto the curved surface to be analyzed.

11. The device according to claim 1 wherein at least two detectors of said plurality of detectors are sensitive for radiation of different wavelengths.

12. The device according to claim 1 wherein said detection means includes at least one detector that is sensitive to infrared light.

13. The device according to claim 1 wherein said detection means is at least one detector that is sensitive to visible light.

14. The device according to claim 1 further including an evaluation means connected with the detection means.

15. A method for the quantified evaluation of a curved surface utilizing a device according to claim 1 including the steps:
    irradiating a curved surface to be analyzed using a first radiation means configured to emit non-collimated light in the spectrum of infrared light;
    irradiating the curved surface to be analyzed using at least one second radiation means configured to emit light in the spectrum of visible light;
    detecting the radiation irradiated onto the curved surface and reflected back from it;
    analyzing light intensities associated with the reflected radiation;
    generating a signal characteristic based on the reflected radiation;
    evaluating the characteristic signal; and
    moving the device along a direction of curvature of the curved surface to be analyzed.

* * * * *